United States Patent
Medema

(10) Patent No.: US 11,207,538 B2
(45) Date of Patent: *Dec. 28, 2021

(54) WEARABLE CARDIOVERTER DEFIBRILLATOR (WCD) SYSTEM WARNING AMBULATORY PATIENT BY WEAK ALERTING SHOCK

(71) Applicant: West Affum Holdings Corp., Grand Cayman (KY)

(72) Inventor: Douglas K. Medema, Everett, WA (US)

(73) Assignee: WEST AFFUM HOLDINGS CORP., Grand Cayman (KY)

(*) Notice: Subject to any disclaimer, the term of this patent is extended or adjusted under 35 U.S.C. 154(b) by 107 days.

This patent is subject to a terminal disclaimer.

(21) Appl. No.: 16/112,545

(22) Filed: Aug. 24, 2018

(65) Prior Publication Data

US 2019/0076666 A1    Mar. 14, 2019

Related U.S. Application Data

(60) Provisional application No. 62/557,713, filed on Sep. 12, 2017.

(51) Int. Cl.
*A61N 1/39*        (2006.01)
*A61N 1/04*        (2006.01)

(52) U.S. Cl.
CPC ......... *A61N 1/3987* (2013.01); *A61N 1/3904* (2017.08); *A61N 1/046* (2013.01);
(Continued)

(58) Field of Classification Search
CPC .. A61N 1/3904; A61N 1/3956; A61N 1/3987; A61N 1/3993; A61N 1/046
See application file for complete search history.

(56) References Cited

U.S. PATENT DOCUMENTS

| 3,724,355 A | 4/1973 | Unger |
| 3,724,455 A | 4/1973 | Unger |

(Continued)

FOREIGN PATENT DOCUMENTS

WO    1998039061 A2    9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Eric D. Bertram
(74) *Attorney, Agent, or Firm* — Spectrum IP Law Group LLC

(57) ABSTRACT

In embodiments, a wearable cardioverter defibrillator (WCD) system is configured to be worn by an ambulatory patient. In the event that the WCD system determines that defibrillation is needed, it delivers a defibrillation shock. To diminish the possibility that the patient will be shocked due to a false positive detection, the WCD system alerts a patient that a defibrillation shock is imminent, and invites them to react to avert it. Alerting may be by a very weak shock, or jolt. Alerting by a jolt can be a last resort warning. An advantage can be that the patient has a higher chance of being alerted by the jolt, especially in the event that the patient is not reacting to other human-perceptible alerts, such as when the patient is riding a motorcycle.

31 Claims, 4 Drawing Sheets

SAMPLE SCENARIO OF JOLTING THE PATIENT FOR WARNING ABOUT IMPENDING DEFIBRILLATION SHOCK

(52) U.S. Cl.
CPC .......... *A61N 1/0484* (2013.01); *A61N 1/0496* (2013.01); *A61N 1/3975* (2013.01); *A61N 1/3993* (2013.01)

(56) References Cited

U.S. PATENT DOCUMENTS

| | | | |
|---|---|---|---|
| 4,583,524 A | 4/1986 | Hutchins | |
| 4,619,265 A | 10/1986 | Morgan et al. | |
| 4,928,690 A * | 5/1990 | Heilman | A61B 5/6831 |
| | | | 600/509 |
| 4,955,381 A | 9/1990 | Way et al. | |
| 5,078,134 A | 1/1992 | Heilman et al. | |
| 5,228,449 A | 7/1993 | Christ et al. | |
| 5,332,400 A * | 7/1994 | Alferness | A61N 1/3925 |
| | | | 607/5 |
| 5,348,008 A | 9/1994 | Bomn et al. | |
| 5,353,793 A | 10/1994 | Bomn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,427,083 B1 | 7/2002 | Owen et al. | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,592,403 B2 | 3/2017 | Sullivan | |
| 9,757,579 B2 * | 9/2017 | Foshee, Jr. | A61N 1/0484 |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 * | 11/2012 | Kaib | G16H 50/30 |
| | | | 340/539.12 |
| 2012/0302860 A1 | 11/2012 | Volpe et al. | |
| 2012/0310315 A1 | 12/2012 | Savage et al. | |
| 2013/0085538 A1 * | 4/2013 | Volpe | A61B 5/7221 |
| | | | 607/6 |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0328472 A1 | 11/2015 | Sullivan et al. | |
| 2016/0004831 A1 | 1/2016 | Carlson et al. | |
| 2016/0074667 A1 * | 3/2016 | Sullivan | A61B 5/6802 |
| | | | 607/6 |
| 2016/0082277 A1 | 3/2016 | Foshee, Jr. et al. | |
| 2017/0056682 A1 * | 3/2017 | Kumar | A61N 1/046 |

OTHER PUBLICATIONS

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

SAMPLE COMPONENTS OF WEARABLE
CARDIOVERTER DEFIBRILLATOR (WCD)
SYSTEM

SAMPLE COMPONENTS OF EXTERNAL DEFIBRILLATOR

SAMPLE SCENARIO OF JOLTING THE PATIENT FOR WARNING ABOUT IMPENDING DEFIBRILLATION SHOCK

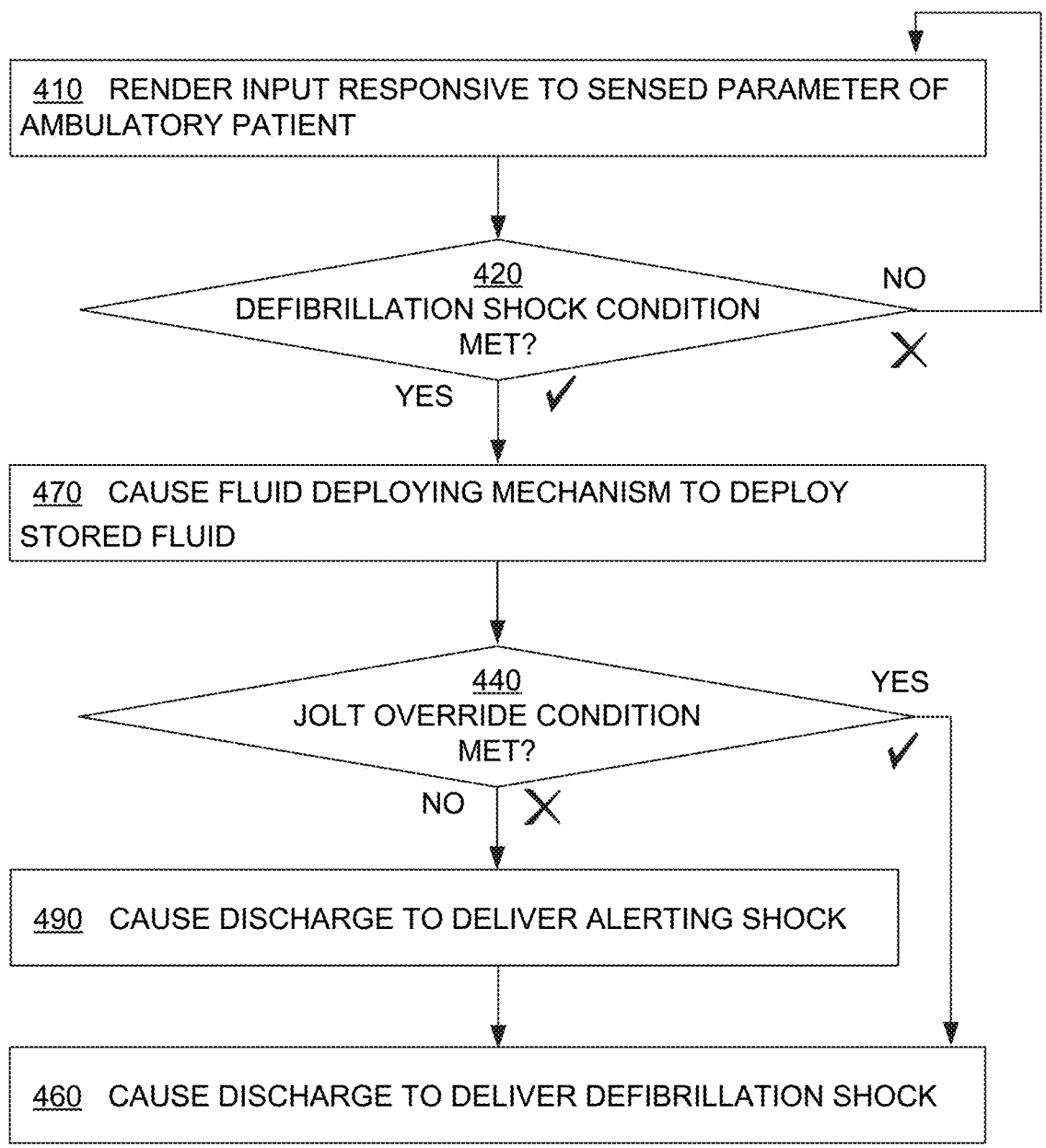
FIG. 4     *METHODS*

WEARABLE CARDIOVERTER DEFIBRILLATOR (WCD) SYSTEM WARNING AMBULATORY PATIENT BY WEAK ALERTING SHOCK

CROSS REFERENCE TO RELATED PATENT APPLICATIONS

This patent application claims priority from U.S. Provisional Patent Application Ser. No. 62/557,713, filed on Sep. 12, 2017.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart, and save their life.

Sometimes the ECG analysis algorithm will determine that defibrillation therapy is required when, in fact, it is not required. Such incidents are generally called false positives. Many times such result from electrical noise on the ECG signal that is an artifact from patient motion or interference from electrostatic sources near the patient.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor(s). This approach in and of itself may also be inventive.

BRIEF SUMMARY

The present description gives instances of wearable cardioverter defibrillator (WCD) systems, storage media that may store programs, and methods, the use of which may help overcome problems and limitations of the prior art.

In embodiments, a wearable cardioverter defibrillator (WCD) system is configured to be worn by an ambulatory patient. In the event that the WCD system determines that defibrillation is needed, it delivers a defibrillation shock. To diminish the possibility that the patient will be shocked due to a false positive detection, the WCD system alerts a patient that a defibrillation shock is imminent, and invites them to react to avert it. Alerting may be by a very weak shock, or jolt.

Alerting by such a weak shock can be a last resort warning. An advantage can be that the patient has a higher chance of being alerted by the jolt, especially in the event that the patient is not reacting to other human-perceptible alerts, such as when the patient is riding a motorcycle.

These and other features and advantages of the claimed invention will become more readily apparent in view of the embodiments described and illustrated in this specification, namely in this written specification and the associated drawings.

BRIEF DESCRIPTION OF THE DRAWINGS

FIG. 4 is a flowchart for illustrating sample methods according to embodiments.

DETAILED DESCRIPTION

As has been mentioned, the present description is about wearable cardioverter defibrillator (WCD) systems, storage media and methods. Embodiments are now described in more detail.

A wearable cardioverter defibrillator (WCD) system according to embodiments may protect an ambulatory patient by electrically restarting their heart if needed. Such a WCD system may have a number of components. These components can be provided separately as modules that can be interconnected, or can be combined with other components, and so on.

Figure 1:
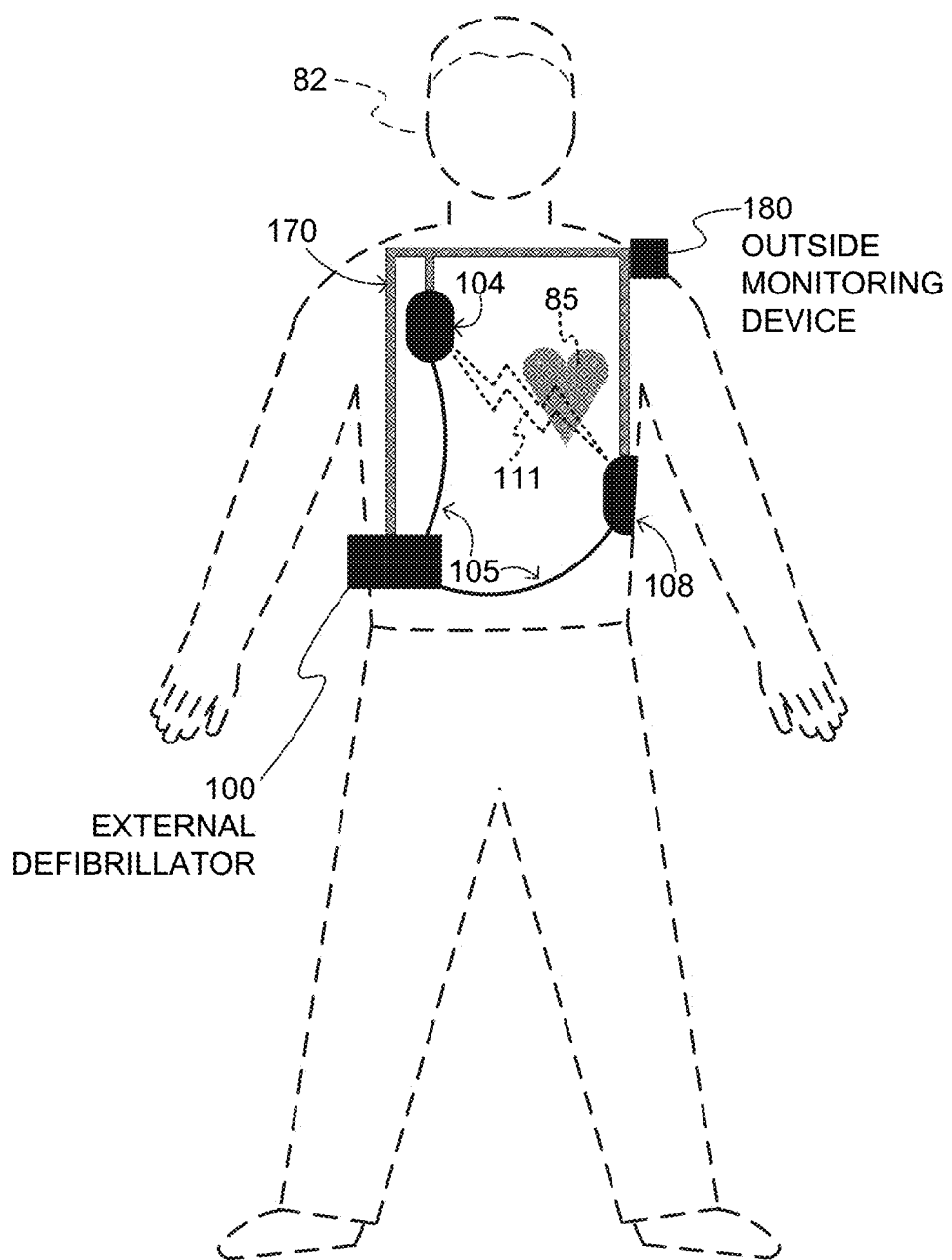
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bed-ridden. While patient 82 may be considered to be also a "user" of the WCD system, this is not a requirement. That is, for example, a user of the wearable cardioverter defibrillator (WCD) may also be a clinician such as a doctor, nurse, emergency medical technician (EMT) or other similarly situated individual (or group of individuals). In some extreme cases a user may be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months.

It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100, and sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108. When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as a informing whether or not a threshold is crossed, and so on. Sometimes these inputs about patient 82 are also called physiological inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since the patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
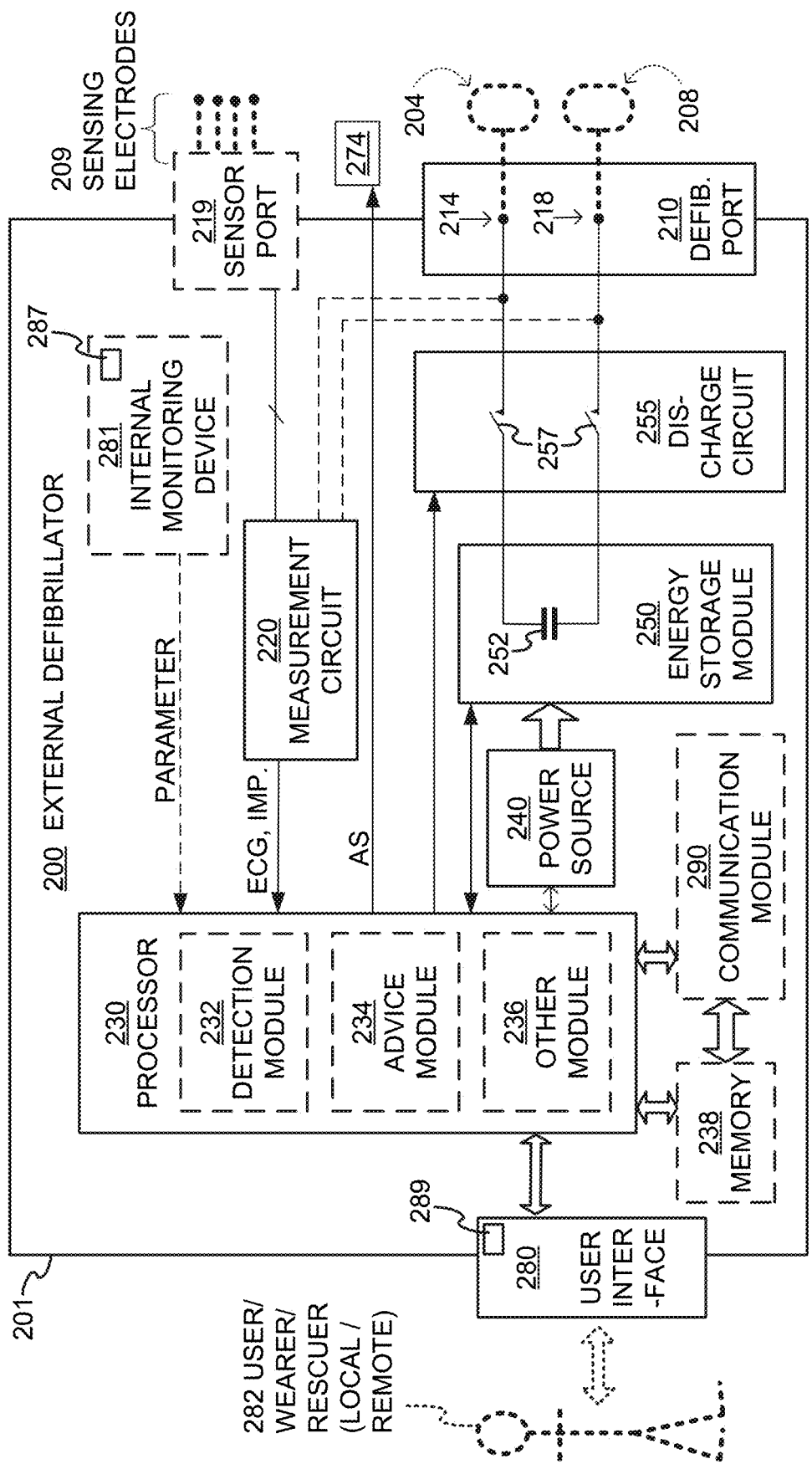
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones such as a sound detector 289, and so on. An input device can be a cancel switch, which is sometimes called an "I am alive" switch or "live man" switch. In some embodiments, actuating the cancel switch creates a cancel input, which in turn prevents the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors as described above.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors and or as taught in U.S. Pat. No. 8,135,462, which is hereby incorporated by reference in its entirety. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281.

A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. Sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAA5), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determining whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be controlled via user interface 280.

A time waveform of the discharge may be controlled by thus controlling discharge circuit 255. The amount of energy of the discharge can be controlled by how much energy storage module has been charged, and also by how long discharge circuit 255 is controlled to remain open.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc.

Defibrillator 200 can optionally include other components.

In some embodiments, a WCD system delivers a weak alerting shock to the patient, for warning the patient. The warning could be for a number of reasons, such as for the patient to react so as to avert an impending defibrillation shock. Examples are now described.

Figure 3:
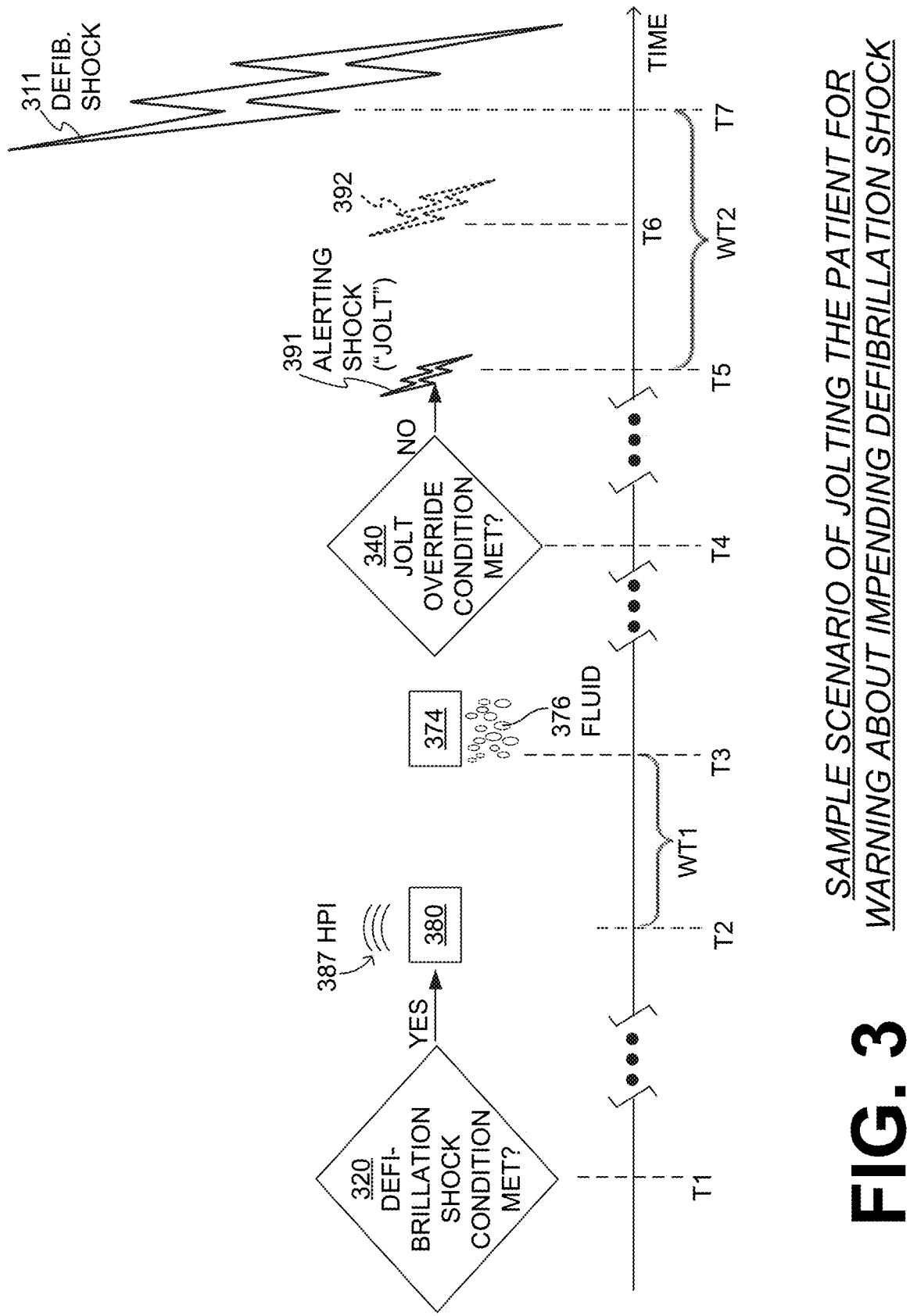
FIG. 3 is a conceptual time diagram of a sample scenario that may take place according to embodiments.

FIG. 3 is a diagram along a time axis. A sample scenario that may take place according to embodiments is described in terms of times T1, T2, . . . , T7. It will be appreciated that this diagram is conceptual in that the time axis is not to scale, and in fact it is interrupted in places; further, concepts are drawn as lasting some time that could be very short, and so on.

At time T1, an operation 320 may be executed that determines whether or not a defibrillation shock criterion is met. The determination of operation 320 may have been made from a parameter of the patient, as describes above. The parameter may include an Electrocardiogram (ECG) signal of the patient, in which case the aforementioned input from which the determination is made may include values of the ECG signal, the ECG signal itself etc.

In this example, the answer to operation 320 is YES. As a result, a defibrillation shock 311 will be delivered, ultimately at time T7 in this example. Defibrillation shock 311 can be as defibrillation shock 111, and can have an energy of at least 50 J (Joule), and more likely at least 150 J and even higher.

A WCD system according to embodiments may try to give the patient a chance to avert the electric shock, for example in the event that the YES answer is a false positive. For example, at time T5, processor 230 may cause, responsive to the defibrillation shock condition being met at operation 320, at least some of the electrical charge stored in energy storage module 250 to be discharged via at least one of electrodes 204, 208 through ambulatory patient 82, so as to deliver to patient 82 an alerting shock 391 at time T5.

In embodiments, alerting shock 391 is delivered via the very system that would deliver defibrillation shock 311. For example, capacitor 252 may be charged some, and then at least some of its charge may be discharged. Alerting shock 391 would have, of course, less energy than defibrillation shock 311. In fact, alerting shock 391 may have an energy between 0.001 J and 20 J, for example somewhat less than 1 J. This amount of energy is enough to lightly jolt the patient, make the patient notice, but not so strong as to cause involuntary muscle movements which could cause the patient to make undesirable movements. This is why alerting shock 391 may also be called a jolt 391. And since alerting shock 391 is delivered responsive to a defibrillation criterion being met, alerting shock 391 should not be confused with a pacing pulse. If, however, the discharge circuit such as an H-bridge has a pacing sub-circuit distinct from a defibrillation sub-circuit, it is preferred that the pacing sub-circuit be used for jolt 391.

In some embodiments, alerting shock 391 can be 0.7 Joules max, with capacitor 252 charged at about 100 volts. If a 50 ohm patient is assumed, then this would decay to less than 10 volts in less than 2 ms. With a 300 ohm patient, the time would be less than 4.5 ms. As such, embodiments do not use special pulse beyond the exponential decay of capacitor 252.

In some embodiments, the feature of alerting shock 391 may be disabled or enabled. For example, the alerting shock might not be delivered responsive to a disable input being received by a user interface of the WCD system. That disable input can be entered by a doctor at the time settings are established for the WCD system, or by the patient in view of starting or ending some activity which by its nature makes the other alarms more or less likely to be noticed.

Alerting shock 391 may be part of a process for warning patient 82 as part of a progressively escalating alarm system. For example, in some embodiments, processor 230 is further configured to cause user interface 280 to emit a warning human-perceptible indication responsive to the determination of operation 320. In the example of FIG. 3, a user interface 380 is shown emitting a since warning human-perceptible indication HP1 387 at time T2, responsive to the YES determination of operation 320. Human-perceptible indication 387 is one intended to be sensed by a person's five senses: the facilities of sight, smell, hearing, taste, and touch. (In contradistinction, alerting shock 391 is of course human-perceptible, but not intended for any of the patient's five senses.) While a single HP1 387 is shown in FIG. 3, a WCD system may actually use a whole sequence of alarms, which escalate. For example, the sequence may include a vibration alert, then tones at low volume, then increasing tones and or voice alarms, and finally all of the alerts at their highest intensity.

After a warning human-perceptible indication is emitted at time T2, the WCD system may wait for a first waiting time WT1, namely until time T3. WT1 could last, for example, 10 seconds.

In such embodiments, alerting shock 391 and defibrillation shock 311 might not be delivered, responsive to a first patient cancel condition being met within first waiting time WT1 after the warning human-perceptible indication is thus emitted. There is a number of ways in which that first patient cancel condition could be met. For example, the first patient cancel condition could be met responsive to a cancel input being received by user interface 280, 380 within first waiting time WT1. Such cancel inputs are described above. In the example of FIG. 3, a cancel input is not received by the user interface.

In some embodiments, a WCD system further includes a fluid reservoir configured to store a fluid, and a fluid deploying mechanism 274. In such embodiments, processor 230 can be further optionally configured to cause fluid deploying mechanism 274 to deploy the stored fluid prior to causing alerting shock 391 to be delivered, so as to facilitate the jolt.

In the specific example of FIG. 3, a fluid deploying mechanism 374 is shown deploying fluid 376 at time T3, which is prior to time T5. This way jolt 391 will be facilitated. In other embodiments, however, the fluid might not be deployed before the jolt, but only before the defibrillation shock.

In some embodiments, processor 230 is further configured to determine whether or not a jolt override condition is met. In such embodiments, alerting shock 391 is not delivered to the patient responsive to the jolt override condition being met.

In the example of FIG. 3, at time T4, an operation 340 may be executed that determines whether or not the jolt override condition is met. In this example, it is not met, and jolt 391 is indeed delivered at time T5.

The jolt override condition may serve where it can be determined that it is pointless to try to get the attention of the patient. There are a number of possibilities.

First, the sensor of the WCD system may include a motion detector 287. For example, motion detector 287 can be configured to output a motion detection signal that indicates an amount of motion sensed by motion detector 287. In such embodiments, the jolt override condition can be determined to exist responsive to an output motion detection signal indicating an amount of motion less than a threshold. For instance, if there is no motion at all, it can be presumed that the patient is suffering from a SCA, and there is no need to jolt them before defibrillating them.

Second, the sensor of the WCD system may include a sound detector within user interface 280. The sound detector can be configured to output a sound detection signal indicative of a sound level sensed by the sound detector. In such embodiments, the jolt override condition can be determined to exist responsive to the output sound detection signal indicating a sound level less than a threshold. For instance, if there is no ambient sound, the patient likely heard HPI 387 at time T2 and did not respond anyway. As such, it can be presumed that the patient is suffering from a SCA, and there is no need to jolt them before defibrillating them.

So, after alerting shock 391 is thus delivered at time T5, the WCD system may wait for a second waiting time WT2 until time T7 to deliver defibrillation shock 311. WT2 could last, for example, 10 seconds. In some embodiments, defibrillation shock 311 is not delivered, responsive to a second patient cancel condition being met within second waiting time WT2 after alerting shock 391 is thus delivered at time T5. The second patient cancel condition can be the same or different as the above-described first patient cancel condition. As such, in embodiments the second patient cancel condition can be met responsive to a cancel input being received by the user interface within second waiting time WT2, and so on. In the example of FIG. 3, the second patient cancel condition is not met, and defibrillation shock 311 is indeed delivered at time T7.

In some embodiments, processor 230 is further configured to cause an other alerting shock to be delivered, for example after the first one. This other alerting shock may have more energy than the first one, in case the patient did not notice the first one. Still, this other alerting shock would be weak, not defibrillation-sized, for example would have energy less than 20 J.

The timing of this other alerting shock is shown in FIG. 3 as taking place at time T6. Still jolt 392 is shown dotted because it does not happen in the scenario of FIG. 3. If it were happening, then the second waiting time WT2 would have to be redefined, then a further new third waiting time would have to be defined after T6 and before T7, and so on.

The devices and/or systems mentioned in this document may perform functions, processes, acts, operations, actions and/or methods. These functions, processes, acts, operations, actions and/or methods may be implemented by one or more devices that include logic circuitry. A single such device can be alternately called a computer, and so on. It may be a standalone device or computer, such as a general purpose computer, or part of a device that has and/or can perform one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description may include flowcharts, display images, algorithms, and symbolic representations of program operations within at least one computer readable medium. An economy may be achieved in that a single set of flowcharts can be used to describe both programs, and also methods. So, while flowcharts describe methods in terms of boxes, they may also concurrently describe programs.

Methods are now described.

FIG. 4 shows a flowchart 400 for describing methods according to embodiments. According to an operation 410, an input may be rendered by the sensor, responsive to the parameter of the ambulatory patient that is sensed by the sensor.

According to another operation 420, it can be determined whether or not a defibrillation shock condition is met. The determination may be from the input of operation 410. A similarity may be observed between operations 420 and 320 in FIG. 3. If, at operation 420 the answer is NO, then execution may return to operation 410.

If, at operation 420 the answer is YES then, according to another, optional operation 470, a fluid deploying mechanism can be caused to deploy a stored fluid, such as fluid 376.

According to another, optional operation 440, it can be determined whether or not a jolt override condition is met. This can be performed as described above.

If, at operation 440 the answer is YES, then according to another operation 460, a defibrillation shock 311, 111 can be caused to be delivered to the ambulatory patient wearing the WCD system. For example, at least some of the electrical charge stored in an energy storage module can be caused to be discharged via at least one of the electrodes through the ambulatory patient, so as to deliver to the patient the defibrillation shock.

If, at operation 440 the answer is NO, then according to another operation 490, an alerting shock 391 can be caused to be delivered to the ambulatory patient wearing the WCD system. For example, at least some of the electrical charge stored in an energy storage module can be caused to be discharged via at least one of the electrodes through the ambulatory patient, so as to deliver to the patient the alerting shock. After that, and after a waiting time T2, execution may proceed to operation 460.

Other variations are possible, for example as described above. For example, the alerting shock might not be delivered responsive to a received disable input. Or, responsive to a second patient cancel condition being met within the second waiting time. Or, responsive to a first patient cancel condition being met within the first waiting time, if a warning human-perceptible indication has been emitted responsive to the YES determination at operation 420. In addition, an other and then an further additional jolt may be delivered, to escalate the warnings, and so on.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system, comprising:
    an energy storage module configured to store an electrical charge via a defibrillation electrode;
    a support structure configured to be worn by an ambulatory patient to maintain the defibrillation electrode on a skin of the ambulatory patient external to a body of the ambulatory patient;
    a sensor configured to sense a parameter of the ambulatory patient via an Electrocardiogram (ECG) electrode separate from the defibrillation electrode and to render an input responsive to the sensed parameter; and
    a processor configured to:
        determine from the input whether a defibrillation shock condition is met,
        provide a first level of warning to the patient, responsive to the defibrillation shock condition being met, about an impending defibrillation shock,
        escalate to a second level of warning to the patient when a jolt override condition is not met by causing at least some of the stored electrical charge to be discharged via the defibrillation electrode through the ambulatory patient to deliver to the skin of the ambulatory patient an alerting shock, when enabled, having an energy between 0.001 joules (J) and 20 J, wherein the processor can be configured, prior to the defibrillation shock condition being met, to enable or disable operation of the alerting shock;
        cause, responsive to the defibrillation shock condition being met and after delivery of the alerting shock, at least some of the stored electrical charge to be discharged via the defibrillation electrode through the ambulatory patient to deliver to the ambulatory patient a defibrillation shock having an energy of at least 50 J; and
        prevent delivery of the defibrillation shock when a cancel input is received after delivery of the alerting shock and before delivery of the defibrillation shock.

2. The WCD system of claim 1, in which
the parameter includes an Electrocardiogram (ECG) signal of the patient; and
the WCD system further comprises a sound detector to detect an ambient sound level, wherein the processor is further configured to deliver the alerting shock when the ambient sound level is greater than a threshold noise level, and to otherwise not deliver the alerting shock.

3. The WCD system of claim 1, further comprising:
a user interface, and in which
the processor is further configured to:
    cause the user interface to emit a warning human-perceptible indication as the first level of waring to the patient, and
the alerting shock and the defibrillation shock are not delivered responsive to a first patient cancel condition being met within a first waiting time after the warning human-perceptible indication is emitted.

4. The WCD system of claim 3, in which
the first patient cancel condition is met responsive to a cancel input being received by the user interface within the first waiting time.

5. The WCD system of claim 3, in which
the defibrillation shock is not delivered responsive to a second patient cancel condition being met within a second waiting time after the alerting shock is thus delivered.

6. The WCD system of claim 5, further comprising:
a user interface, and in which
the second patient cancel condition is met responsive to a cancel input being received by the user interface within the second waiting time.

7. The WCD system of claim 1, further comprising:
a fluid reservoir configured to store a fluid; and
a fluid deploying mechanism, and in which
the processor is further configured to cause the fluid deploying mechanism to deploy the stored fluid prior to causing the alerting shock to be delivered.

8. The WCD system of claim 1, in which
the alerting shock is not delivered to the patient responsive to the jolt override condition being met.

9. The WCD system of claim 8, in which
the sensor includes a motion detector configured to output a motion detection signal indicative of an amount of motion sensed by the motion detector, and
the jolt override condition is determined to exist responsive to the output motion detection signal indicating an amount of motion less than a threshold.

10. The WCD system of claim 8, further comprising:
a user interface, and in which
the user interface includes a sound detector configured to output a sound detection signal indicative of a sound level sensed by the sound detector, and
the jolt override condition is determined to exist responsive to the output sound detection signal indicating a sound level less than a threshold.

11. The WCD system of claim 1, in which
the processor is further configured to:
cause at least some of the stored electrical charge to be discharged through the ambulatory patient to deliver to the ambulatory patient another alerting shock having an energy less than 20 J.

12. The WCD system of claim 1, wherein the energy of the alerting shock is less than 0.1 joule.

13. The WCD system of claim 1, wherein the energy of the alerting shock is one percent or less of the energy of the defibrillation shock.

14. The WCD system of claim 1, further comprising a user interface coupled with the processor, wherein operation of the alerting shock can be enabled or disabled via the user interface based at least in part on an activity to be engaged in by the ambulatory patient.

15. A non-transitory computer-readable storage medium storing one or more programs which, when executed by at least one processor of a wearable cardioverter defibrillator (WCD) system, the WCD system including an energy storage module storing an electrical charge, a defibrillation electrode, a support structure worn by an ambulatory patient to maintain the defibrillation electrode on a skin of the ambulatory patient external to a body of the ambulatory patient, and a sensor sensing a parameter of the ambulatory patient via an Electrocardiogram (ECG) electrode separate from the defibrillation electrode and rendering an input responsive to the sensed parameter, these one or more programs result in operations comprising:
enabling or disabling operation of the alerting shock prior to a defibrillation shock condition being met;
determining from the input whether the defibrillation shock condition is met;
providing a first level of warning to the patient, responsive to the defibrillation shock condition being met, about an impending defibrillation shock,
escalating to a second level of warning to the patient when a jolt override condition is not met by causing at least some of the stored electrical charge to be discharged via the defibrillation electrode through the ambulatory patient to deliver to the skin of the ambulatory patient an alerting shock, when enabled, having an energy between 0.001 joules (J) and 20 J;
causing, responsive to the defibrillation shock condition being met and after delivery of the alerting shock, at least some of the stored electrical charge to be discharged via the defibrillation electrode through the ambulatory patient to deliver to the ambulatory patient a defibrillation shock having an energy of at least 50 J; and
preventing delivery of the defibrillation shock when a cancel input is received after delivery of the alerting shock and before delivery of the defibrillation shock.

16. The non-transitory computer-readable storage medium of claim 15, wherein the energy of the alerting shock is less than 0.1 joule.

17. The non-transitory computer-readable storage medium of claim 15, wherein the energy of the alerting shock is one percent or less of the energy of the defibrillation shock.

18. A method for a wearable cardioverter defibrillator (WCD) system, the WCD system including an energy storage module storing an electrical charge, a defibrillation electrode, a support structure worn by an ambulatory patient to maintain the defibrillation electrode on a skin of the ambulatory patient external to a body of the ambulatory patient, a sensor sensing a parameter of the ambulatory patient via an Electrocardiogram (ECG) electrode separate from the defibrillation electrode, and a processor, the method comprising:
enabling or disabling operation of the alerting shock prior to a defibrillation shock condition being met;
rendering, by the sensor, an input responsive to the sensed parameter of the ambulatory patient;
determining from the input whether the defibrillation shock condition is met;
providing a first level of warning to the patient, responsive to the defibrillation shock condition being met, about an impending defibrillation shock,
escalating to a second level of warning to the patient when a jolt override condition is not met by causing at least some of the stored electrical charge to be discharged via the defibrillation electrode through the ambulatory patient to deliver to the skin of the ambulatory patient an alerting shock, when enabled, having an energy between 0.001 joules (J) and 20 J;
causing, responsive to the defibrillation shock condition being met and after delivery of the alerting shock, at least some of the stored electrical charge to be discharged via the defibrillation electrode through the ambulatory patient to deliver to the ambulatory patient a defibrillation shock having an energy of at least 50 J; and
preventing delivery of the defibrillation shock when a cancel input is received after delivery of the alerting shock and before delivery of the defibrillation shock.

19. The method of claim 18, in which
the parameter includes an Electrocardiogram (ECG) signal of the patient; and
further comprising delivering the alerting shock when an ambient sound level detected by a sound detector of the WCD system is greater than a threshold noise level, and otherwise not delivering the alerting shock.

20. The method of claim 18, in which
the WCD system further includes a user interface, and the alerting shock is not delivered responsive to a disable input being received by the user interface.

21. The method of claim 18, in which
the WCD system further includes a user interface, and further comprising:
causing the user interface to emit a warning human-perceptible indication as the first level of waring to the patient, and
in which the alerting shock and the defibrillation shock are not delivered responsive to a first patient cancel condition being met within a first waiting time after the warning human-perceptible indication is thus emitted.

22. The method of claim 21, in which
the first patient cancel condition is met responsive to a cancel input being received by the user interface within the first waiting time.

23. The method of claim 21, in which
the defibrillation shock is not delivered responsive to a second patient cancel condition being met within a second waiting time after the alerting shock is thus delivered.

24. The method of claim 23, in which
the WCD system further includes a user interface, and
the second patient cancel condition is met responsive to a cancel input being received by the user interface within the second waiting time.

25. The method of claim 18, in which
the WCD system further includes a fluid reservoir storing a fluid and a fluid deploying mechanism, and
further comprising:
causing the fluid deploying mechanism to deploy the stored fluid prior to causing the alerting shock to be delivered.

26. The method of claim 18, wherein the alerting shock is not delivered to the patient responsive to the jolt override condition being met.

27. The method of claim 26, in which
the sensor includes a motion detector outputting a motion detection signal indicative of an amount of motion sensed by the motion detector, and
the jolt override condition is determined to exist responsive to the output motion detection signal indicating an amount of motion less than a threshold.

28. The method of claim 26, in which
the WCD system further includes a user interface,
the user interface includes a sound detector outputting a sound detection signal indicative of a sound level sensed by the sound detector, and
the jolt override condition is determined to exist responsive to the output sound detection signal indicating a sound level less than a threshold.

29. The method of claim 18, further comprising
causing at least some of the stored electrical charge to be discharged through the ambulatory patient to deliver to the ambulatory patient another alerting shock having an energy less than 20 J.

30. The method of claim 18, wherein the energy of the alerting shock is less than 0.1 joule.

31. The method of claim 18, wherein the energy of the alerting shock is one percent or less of the energy of the defibrillation shock.

* * * * *